United States Patent
Khowdiary et al.

(10) Patent No.: US 10,125,160 B1
(45) Date of Patent: Nov. 13, 2018

(54) METHOD OF MAKING COBALT AND PLATINUM BASED SURFACTANTS AND USING FOR CANCER THERAPY

(71) Applicant: Umm Al-Qura University, Makkah (SA)

(72) Inventors: Manal Mohamed Khowdiary, Makkah (SA); Ammona Salem Mohamed, Makkah (SA); Moshera Zaki Mohamed, Makkah (SA)

(73) Assignee: Umm-Al-Qura University, Makkah (SA)

( * ) Notice: Subject to any disclaimer, the term of this patent is extended or adjusted under 35 U.S.C. 154(b) by 0 days.

(21) Appl. No.: 14/605,091

(22) Filed: Jan. 26, 2015

(51) Int. Cl.
*A61P 35/00* (2006.01)
*C07F 15/00* (2006.01)
*C07F 15/06* (2006.01)

(52) U.S. Cl.
CPC .............. *C07F 15/06* (2013.01); *A61P 35/00* (2018.01); *C07F 15/0086* (2013.01)

(58) Field of Classification Search
CPC ....... C07F 15/06; C07F 15/0086; A61P 35/00
See application file for complete search history.

(56) References Cited

U.S. PATENT DOCUMENTS

2017/0007642 A1* 1/2017 Khowdiary ............ A01N 59/02

OTHER PUBLICATIONS

Adawy et al. "Structure and Biological Behaviors of Some Metallo Cationic Surfactants" J. Surfact. Deterg. 2013, 16, 709-715. (Year: 2013).*

* cited by examiner

*Primary Examiner* — Amanda L Aguirre
(74) *Attorney, Agent, or Firm* — Geeta Kadambi; Riddhi IP LLC

(57) ABSTRACT

A method of making benzidine hydrogen selenite complex with Cobalt and Platinum as surfactants is discussed. The resultant benzidine hydrogen selenite complex with either Cobalt or Platinum was characterized for its unique and superior properties. The complexes were characterized by elemental analysis, FTIR, and spectroscopy. The critical micelle concentration and thermodynamic parameters were calculated. The Values of IC50 were also calculated for the prepared complexes as well as their parent complex. The method of using the benzidine hydrogen selenite complex with cobalt and platinum as an antitumor agent to treat cancer is also demonstrated.

16 Claims, 3 Drawing Sheets

METHOD OF MAKING COBALT AND PLATINUM BASED SURFACTANTS AND USING FOR CANCER THERAPY

FIELD OF TECHNOLOGY

This disclosure relates generally to a method of making and using a benzidine surfactant complex to reduce cell viability. More specifically making a Cobalt or Palladium with benzidine hydrogen selenite complex and used for reducing tumor size or cell viability is disclosed.

BACKGROUND

Studies on the chemistry of metallomicelles have received a sustained high level of attention from the scientific community for the last few years (Walker G. W. et. al. 2003) due to their relevance in various redox processes in biological systems, and acting as promising agents for anthelmintic (Behm, C. A.1993), antiparasitic and antibiotics. The metal-surfactant complex is a special type of surfactant, where a coordination complex (containing a central metal ion with surrounding ligands coordinated to the metal) acts as the surfactant. In these surfactants the metal complex entity containing the central metal ion with its primary coordination sphere acts as the head group and the hydrophobic entity of one or more ligands acts as the tail part. It is argued that the high charge and size of the head group of the complex having long paraffin tails; detergent-like characteristics are able to penetrate biological membranes and destabilize the exterior membrane of the organism (Fendler, J. H et. al., 1982). Several platinum complexes have been synthesized in an attempt to find new complex that show antitumor properties, less severe side effects, and that can overcome cellular resistance (Hambley, T. W. 2001). Despite all efforts, only a few compounds have reached clinical use and still present severe side effects. There is a need for novel drug that is required to combat cancer prevention and cure.

SUMMARY

The invention discloses a method of making and using a benzidine based surfactant as antitumor agent. More specifically making Cobalt (Co) and/or Platinum (Pt) with benzidine hydrogen selenite as complexes and its use to reduce cell viability by creating hypoxia is disclosed.

In one embodiment, a method of making the benzidine hydrogen selenite complex (parent complex (Ia)) is described. In another embodiment, a method of making the benzidine hydrogen selenite complex with Cobalt (Co) (parent Co (Ib) is described. In another embodiment, a method of making the benzidine hydrogen selenite complex with Platinum (Pt) (parent Pt (Ic)) is described.

In one embodiment, characterization of the benzidine hydrogen selenite complex with Co/Pt is performed to prove superior functional qualities of the complex having an antitumor agent property is described.

In one embodiment, cancer cell lines of various concentration and types were treated with the benzidine hydrogen selenite complex either with Co or Pt and antitumor activity was determined.

In one embodiment, reduction of cell viability using the benzidine hydrogen selenite complex with Co/Pt is performed to demonstrate cellular hypoxia and resultant cell death.

Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Figure 1:
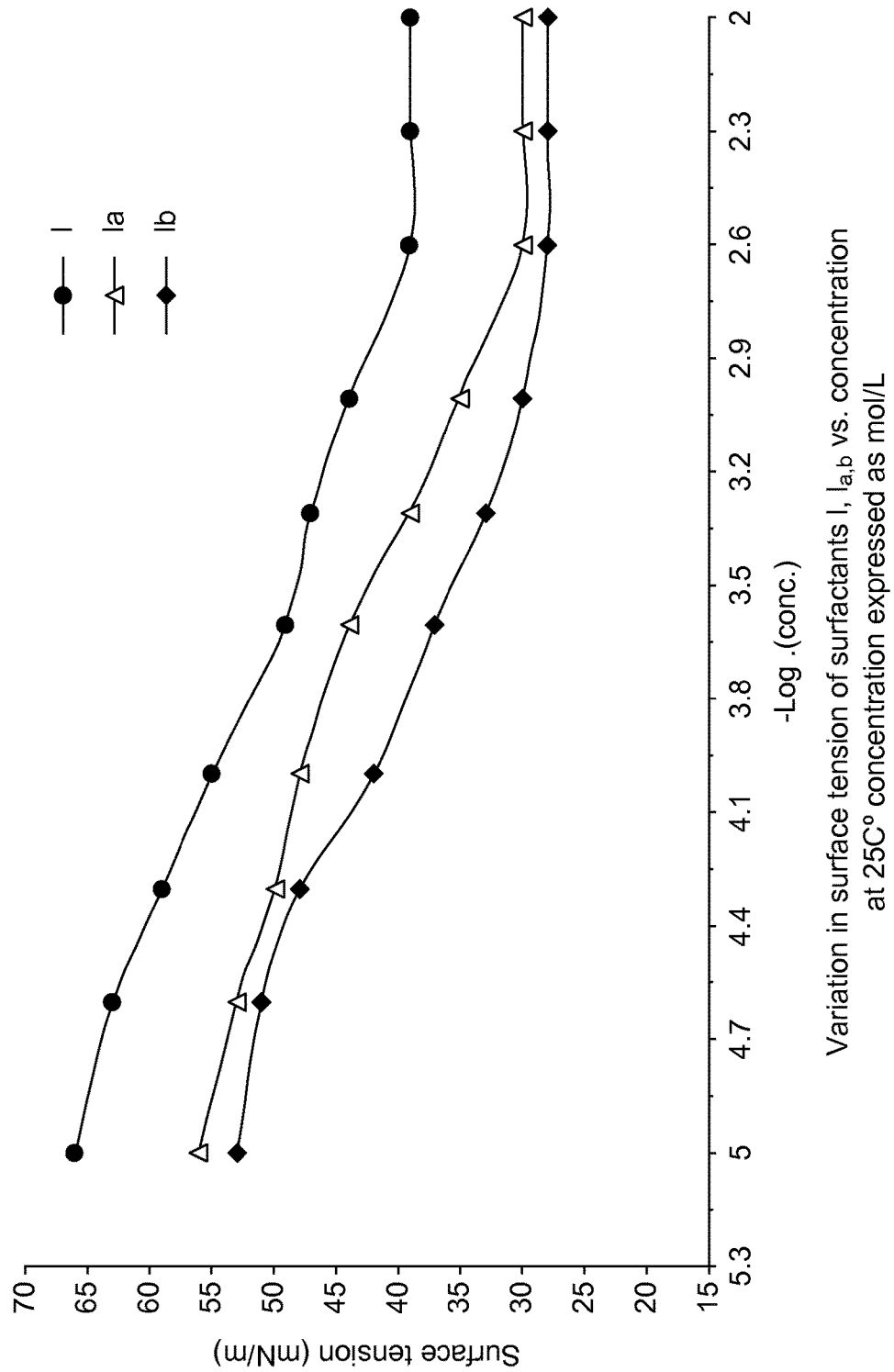
FIG. 1 shows the variation in surface tension of parent complex (Ia), parent complex with Co (Ib), and parent complex with Pt (Ic) at various concentrations at 25° C. is shown.

Other features of the present embodiments will be apparent from the accompanying the detailed description that follows.

DETAILED DESCRIPTION

In this invention a method to make the parent complex, parent complex with Co, and parent complex with Pt is discussed. The method of using the parent complex, parent complex with Co, and parent complex with Pt for inhibiting cell viability in mammalian cells is disclosed.

In this disclosure the method of making, characterization and determination of critical micelle concentration values of the parent complex with Co and parent complex with Pt with simple aromatic diamines is discussed. The outcome of their possible antitumor activity is also disclosed.

Synthesis of N-Decanoylbenzidine:

A solution of decanoic acid (0.02 mol) in xylene (50 mL) was added drop wise by syringe to a solution of benzidine (2.06 g, 0.02 mol) in xylene (25 mL) under reflux. After addition was complete (1 h), the reaction mixture was refluxed for 4 h. After removing xylene, the residue was recrystallized using ethyl acetate to give N-decanoylbenzidine.

Synthesis of N-Decanoylbenzidinum Hydrogen Selenite:

Stoichiometric amounts of selenious acid were mixed with N-decanoylbenzidine at room temperature in ethyl alcohol and then stirred until the precipitation stopped. The precipitant was filtered, washed by ethyl alcohol, and then recrystallized by diethyl ether (crystallization solvent 2) as N-decanoylbenzidinum hydrogen selenite (parent complex) (benzidinium hydrogen selenite complexes). The product is designated as parent complex and has the general formula: $RN^+H_3HSeO_3$. Where

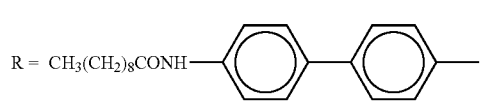

(Eq 1)

$R = CH_3(CH_2)_8CONH-$

Synthesis of Cobalt or Platinum (II) Hydrogen Selenite Dihydrate:

For obtaining cobalt (II) or platinum hydrogen selenite dihydrate, selenius acid $H_2SeO_3$ was reacted with basic metal (II) carbonate $M(OH_2)_2CO_3$, which was prepared by mixing aqueous solution and equimolar amounts of $MCl_2$ and $Na_2CO_3$. The precipitate was washed till the absence of foreign ions.

An aqueous solution of $H_2SeO_3$ 2 g in 10 ml water was added to a warm solution of freshly prepared Cocarbonate 1.28 g in 10 ml water. The obtained solution was filtered and kept at room temperature for crystallization. After 24 hour, crystalline prisms of blue color were formed. The temperature of removal of 2 molecules of water was 100-110° C.

Synthesis of Benzidinium Hydrogen Selenite Complexes with Cobalt and Platinum:

Benzidinium hydrogen selenite complexes with Cobalt or Platinum were prepared by refluxing (0.2 mol) of N-decanoylbenzidinum hydrogen selenite (parent complex) with (0.1 mol) of Cobalt or Platinum hydrogen selenite previously prepared. The products were purified and recrystalized three times in petroleum ether and then washed with diethyl ether. The products were kept in desiccator. The products were designated as (Parent, parent Co, parent Pt).

$$2RN^+H_3(HSeO_3)^- + M(HSeO_3)_2 \rightarrow [RNH_3]^+ 2M [HSeO_3]^{-4} \quad (Eq\ 2)$$

The general formula for the metal complexes is as follows:

$$[RN^+H_3]_2[M(HSeO_3)_4]^{-2} \text{ where } M: Co^{+2} \text{ or } Pt^{+2}. \quad (Eq\ 3)$$

Method of Analysis:

The elemental analysis for the obtained surfactants was carried out using Elemental Analyzer Model Vario Elemental (Table 1). The measurements were carried out in micro Analytical Center, Faculty of Science, Cairo University.

TABLE 1

Elemental analysis for the benzidinium hydrogen selenite surfactants

| Product | M. wt | C % Calc. | C % Found | H % Calc. | H % Found | N % Calc. | N % Found |
|---|---|---|---|---|---|---|---|
| Parent | 467.46 | 56.47 | 56.36 | 6.85 | 7.02 | 5.99 | 6.23 |
| Parent Co | 1248.93 | 42.28 | 42.41 | 5.28 | 5.63 | 4.48 | 5.34 |
| Parent Pt | 1385 | 38.12 | 38.41 | 4.77 | 4.93 | 4.04 | 4.56 |

Infrared spectra for prepared surfactants were measured using Avatar 230 FTIR spectrophotometer to measure intensity of absorption bands for the prepared surfactants (Table 2). The measurements were carried out in Egyptian Petroleum Research Institute.

TABLE 2

Characteristic peaks of the prepared surfactants such as parent, parent with Co, parent with Pt.

| | | Wave no. (cm$^{-1}$) | | |
|---|---|---|---|---|
| Function group | | Parent | Parent Co | Parent Pt |
| CH$_2$ | Multible (CH$_2$) rock | 747 | 725 | 726 |
| | Asymmetric bending | 1463 | 1467 | 1487 |
| | Asymmetric stretch | 2966 | 2921 | 2922 |
| CH$_3$ | Symmetric bending | 1406 | 1409 | 1397 |
| | Symmetric stretch | 2855 | 2852 | 2851 |
| | Ammonium ion (RN$^+$H$_3$) | 2373 | 2370 | 2370 |
| | Co—N | — | 571 | — |
| | Pt—N | — | — | 577 |

Atomic Absorption Spectrometer (AAS) measurements for cobalt and platinum analyses were performed with AAS (Flame absorption) PerkinElmer; the detection limits for this analysis are 0.005 g/20 ml for platinum and 0.003 g/20 ml for cobalt.

TABLE 3

The AAS results for Co$^{2+}$ and Pt$^{2+}$ benzidinium products

| Sample | Concentration (PPM) | Experimental error % |
|---|---|---|
| parent Co | 9.5 | 0.005 |
| parent Pt | 8.7 | 0.013 |

AAS results confirmed the prepared complex, since there is no significant error percent between the expected and the experimental values.

Surface Tension and Critical Micelle Concentration:

Surface tension values of the synthesized complex solutions (parent complex, parent complex with Co, parent complex with Pt) were obtained at 30°C using Du-Nouy Tensiometer (Kruss K6 Type 4851) with a platinum ring. Apparent surface tension was measured about five times for the sample within 2 min interval between each reading. The averages of five determinations were plotted against −log C without any correction. The critical micelle concentration values were determined from the plot of surface tension versus concentration.

Potential Cytotoxicity Measurements by SRB Assay:

Potential cytotoxicity of the complex was tested using the method of Skehan et al. (1990). The tumor cell lines: MCF$_7$ (Breast carcinoma), HEPG$_2$ (liver carcinoma), (10$^4$ cells/well) had been supplied from National Cancer Institute Cairo Egypt, were plated in 96-multiwell plat for 24 h before treatment with the compounds to allow attachment of cell to the wall of the plate.

Different concentrations of the complexes under test (0, 1, 2.5, Sand 10 µg/ml) were added to the cell-monolayer (parent complex, parent complex with Co, parent complex with Pt). Triplicate wells were prepared for each individual dose. Monolayer cells were incubated with the complex for 48 h at 37 C° and in atmosphere of 5% CO$_2$. After 48 h, Cells were fixed, washed and stained with Sulfurhodamine B stain. Excess stain was washed with acetic acid and attached stain was recovered with Tris EDTA buffer. Color intensity was measured in an ELISA reader. The relation between surviving fraction and drug concentration is plotted to get the survival curve of each tumor cell line after the specified compound was added.

Surface-Active Properties of the Prepared Surfactants:

FIG. 1) shows plots of surface tension ($\gamma$) vs. −log of surfactants concentration for all surfactant homologs (parent complex, parent complex with Co, parent complex with Pt). Table 4 summarizes the surface-active parameters such as critical micelle concentration (CMC), $\gamma_{CMC}$, and pC20 (the surfactant concentration required to reduce the surface tension of the solvent by 20 mN/m) determined from the curves of FIG. 1. Values of $\Gamma_{max}$ (the surface excess concentration of surfactant) and $A_{min}$ (interfacial area occupied by the surfactant molecules) were calculated using the Gibbs adsorption equation:

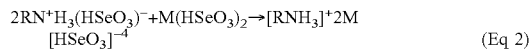

$$\Gamma_{max} = \frac{-1}{RT}\left(\frac{d\gamma}{d\ln c}\right) \quad (Eq\ 4)$$

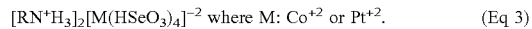

$$A_{min} = 10^{16}/N\ \Gamma_{max} \quad (Eq\ 5)$$

Where ($\delta\gamma/\delta$ log C) is the maximum slope in each case; T is absolute temperature; R=8.31 J/mol and N is Avogadro's number. The standard free energy of micellization ($\Delta G°_{mic}$) is calculated from the equation:

$$\Delta G°_{mic} = RT \ln CMC \quad (Eq\ 7)$$

The standard free energy of adsorption ($\Delta G°_{ads}$) is calculated according to the following equation:

$$\Delta G°_{ads} = \Delta G°_{mic} - \Pi_{CMC} A_{min} \quad \text{(Eq 8)}$$

Both $\Delta G°_{mic}$ and $\Delta G°_{ads}$ become significantly negative (Table 4).

TABLE 4

The critical micelle concentration (CMC) and surface parameters of surfactants:

| Comp. | CMC × $10^{-3}$ | $\gamma_{CMC}$ (mN/m) | $\Pi_{CMC}$ (mN/m) | $P_{C20}$ (Mole/L) | $\Gamma_{max} \times 10^{-11}$ (Mole/cm$^2$) | $A_{min}$ (nm$^2$) | $\Delta G_{ads}$ KJ\mol | $\Delta G_{mic}$ KJ\mol |
|---|---|---|---|---|---|---|---|---|
| parent | 3.76 | 39 | 33 | 3.50 | 9.1 | 1.80 | −64.21 | −27.64 |
| parent Co | 2.50 | 30 | 42 | 4.25 | 8.7 | 1.91 | −76.93 | −29.63 |
| parent Pt | 1.78 | 28 | 44 | 4.42 | 8.3 | 2.01 | −84.34 | −31.34 |

Antitumor Action of the Prepared Compound:

Cobalt and Platinum benzidinium hydrogen selenite complexes as well as their parent were investigated as potential selective, anticancer drugs. These complexes were tested in vitro on human two monolayer tumor cell lines: MCF7 (Breast carcinoma) and HEPG2 (liver carcinoma). The results of the cytotoxic activity on human tumor cell lines were determined according to the dose values of drug exposure for cell lines to reduce survival to 50% (Ic50). The experimental results recorded in Table (5) and plots of surviving fraction versus concentration in µg in FIGS. 2, 3).

TABLE 5

Cytotoxic activity of the prepared complex on human cell line:

| | Cell lines | |
|---|---|---|
| Sample | MCF7 (IC50) µg | HEPG2 (IC50) µg |
| parent | −Ve | −Ve |
| parent Co | 0.60 | 0.94 |
| parent Pt | 0.47 | 1.41 |

Figure 2:
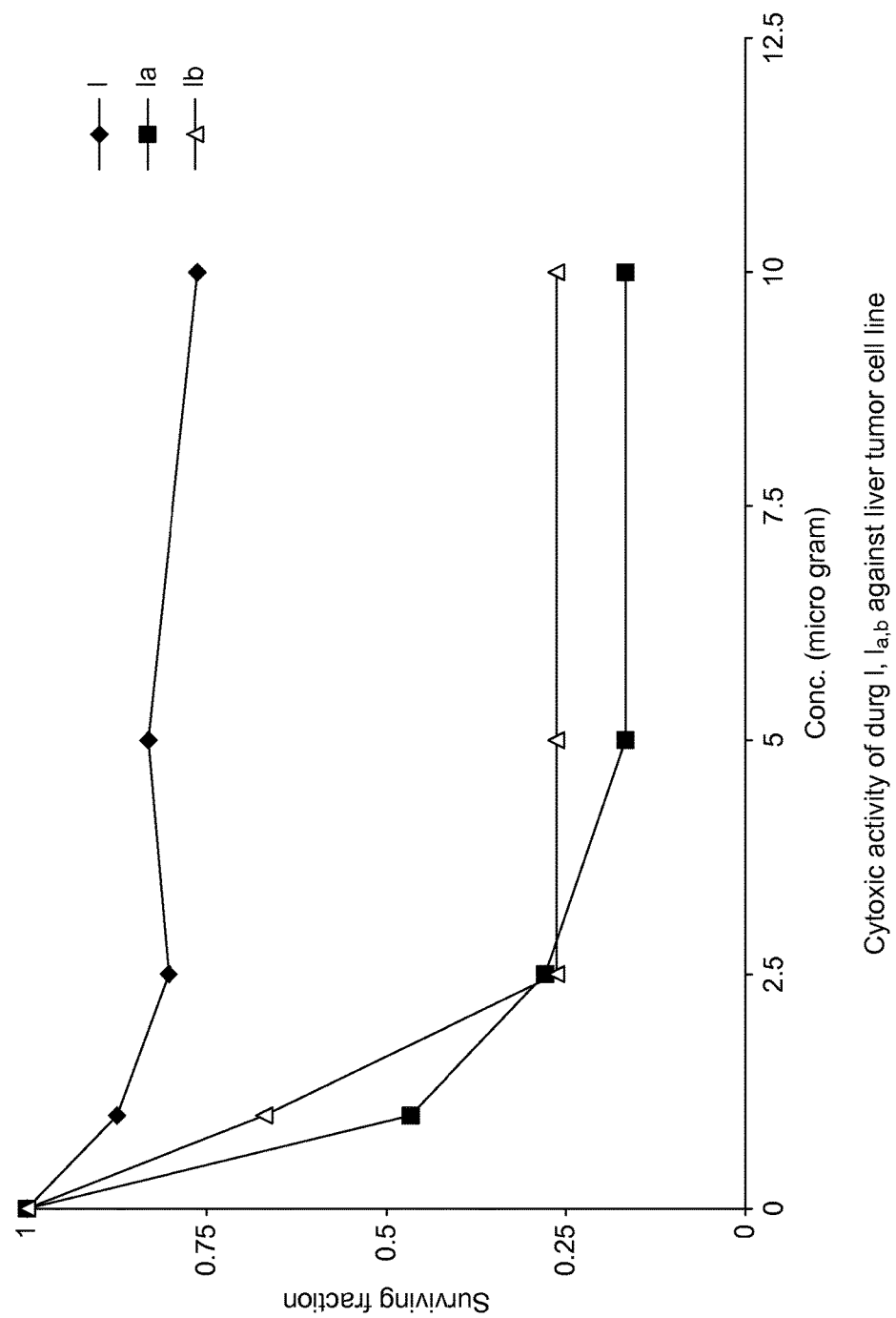
FIG. 2 shows the cytotoxic activity of parent complex, parent complex with Co, and parent complex with Pt in liver tumor cell lines.
Figure 3:
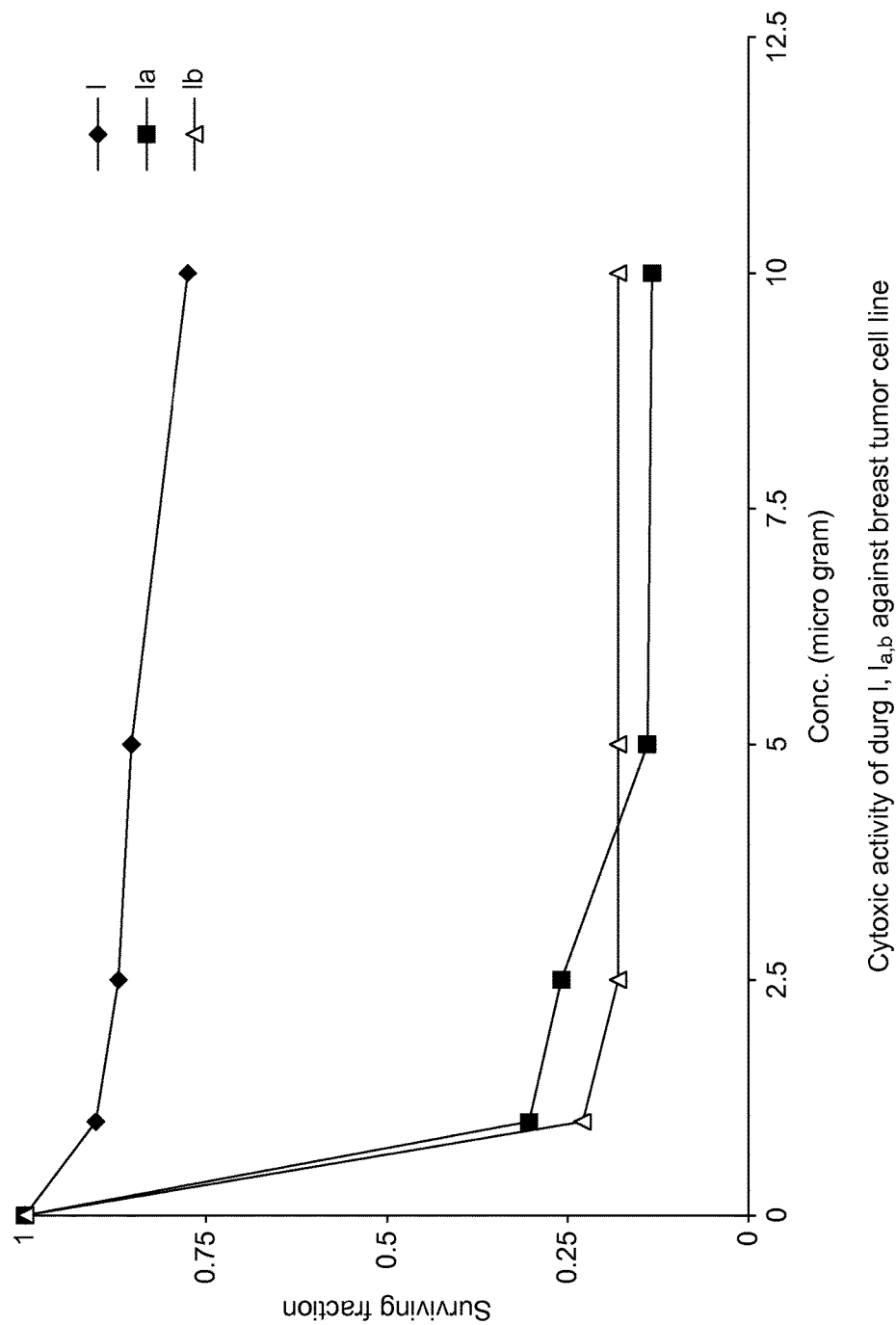
FIG. 3 shows the cytotoxic activity of parent complex (Ia), parent complex with Co (Ib), and parent complex with Pt (Ic) in breast tumor cell lines.

From the results recorded in Table (5) and FIGS. 2,3), parent compound (I) has no effect, while platinum ($I_a$) and cobalt ($I_b$) complex tested exhibited high activity in vitro system on the tumor cell line investigated, parent complex with Co has cytotoxic effect on MCF7 and HEPG2 the dose of it at which the survival reduction to 50% is (Ic50=0.60 and 0.94 µg/ml), respectively, also parent complex with Pt has the cytotoxic effect on MCF7 and HEPG2 (Ic50=0.47 and 1.41) respectively. This comes from the fact that these complexes have a capacity to reduce the energy status in tumors as well as enhance the tumor hypoxia which also influences their antitumor activities. It may be also concluded that the level of cellular damage inflicted by these complexes depends on the nature of their axial ligands.

The novel chemical compound and its therapeutic value are specifically developed to create an antitumor agent in this invention. In addition, it will be appreciated that the various composition of the parent compound, parent compound with Co, and parent compound with Pt and method of making the parent compound, parent compound with Co, and parent compound with Pt disclosed herein may be embodied using means for achieving the various combinations of material and concentrations. Accordingly, the specification and drawings are to be regarded in an illustrative rather than a restrictive sense.

What is claimed is:

1. A method, comprising:
    adding a Decanoic acid (in xylene solution) drop wise to a solution of benzidine in xylene to form a N-decanoyl-benzidine solution;
    mixing the N-decanoylbenzidine in ethyl alcohol with selenious acid to form a N-decanoylbenzidinium hydrogen selenite solution; and
    refluxing the N-decanoylbenzidinium hydrogen selenite solution with either a platinum or cobalt to form a platinum benzidinium hydrogen selenite complex and a cobalt benzidinium hydrogen selenite complex having a critical micelle concentration, a specific tumor reduction rate at a specific concentration for a specific cancer cell line.

2. The method of claim 1, wherein the critical micelle concentration is 2.5 mmol/L for the cobalt benzidinium hydrogen selenite complex.

3. The method of claim 1, wherein the critical micelle concentration is 1.78 for the platinum benzidinium hydrogen selenite complex.

4. The method of claim 1, wherein the tumor reduction rate is 50% for the platinum benzidinium hydrogen selenite complex and the cobalt benzidinium hydrogen selenite complex.

5. The method of claim 1, wherein the specific concentration of the platinum benzidinium hydrogen selenite complex and the cobalt benzidinium hydrogen selenite complex is between 2.5 to 10 ug/ml.

6. The method of claim 1, wherein the specific cell line is liver carcinoma cell line or breast carcinoma cell line.

7. A method, comprising:
    forming a N-decanoylbenzidiniurr solution by adding a Decanoic acid (in xylene solution) drop wise to a solution of benzidine in xylene;
    forming a N-decanoylbenzidinium hydrogen selenite by mixing the N-decanoylbenzidine in ethyl alcohol with selenious acid; and
    refluxing the N-decanoylbenzidinum hydrogen selenite with a cobalt to form a cobalt benzidinium hydrogen selenite complex having a critical micelle concentration, a specific tumor reduction rate at a specific concentration for a specific cancer cell line.

8. The method of claim 7, wherein the critical micelle concentration is 2.5 mmol/L.

9. The method of claim 7, wherein the tumor reduction rate is 50%.

10. The method of claim 7, wherein the specific concentration is between 2.5 to 10 ug/ml.

11. The method of claim 7, wherein the specific cell line is liver carcinoma cell line or breast carcinoma cell line.

12. A method, comprising:
    adding a Decanoic acid (in xylene solution) drop wise to a solution of benzidine in xylene to form a N-decanoyl-benzidine solution;

mixing the N-decanoylbenzidine in ethyl alcohol with selenious acid to form a N-decanoylbenzidinium hydrogen selenite solution; and refluxing the N-decanoylbenzidinium hydrogen selenite solution with either a platinum to form a platinum benzidinium hydrogen selenite complex having a critical micelle concentration, a specific tumor reduction rate at a specific concentration for a specific cancer cell line.

13. The method of claim 12, wherein the tumor reduction rate is 50%.

14. The method of claim 12, wherein the specific concentration is between 2.5 to 10 ug/ml.

15. The method of claim 12, wherein the specific cell line is liver carcinoma cell line or breast carcinoma cell line.

16. The method of claim 12, wherein the critical micelle concentration is 1.78 mmol/L for the platinum benzidinium hydrogen selenite complex.

* * * * *